(12) United States Patent
Chen

(10) Patent No.: US 11,554,199 B1
(45) Date of Patent: Jan. 17, 2023

(54) ASSEMBLING-FACILITATED BREAST PUMP

(71) Applicant: SHENZHEN LUTEJIACHENG NETWORK TECHNOLOGY CO., LTD., Shenzhen (CN)

(72) Inventor: Wanyuan Chen, Shenzhen (CN)

( * ) Notice: Subject to any disclaimer, the term of this patent is extended or adjusted under 35 U.S.C. 154(b) by 0 days.

(21) Appl. No.: 17/837,193

(22) Filed: Jun. 10, 2022

(51) Int. Cl.
*A61M 1/06* (2006.01)

(52) U.S. Cl.
CPC ..... *A61M 1/067* (2021.05); *A61M 2205/0216* (2013.01)

(58) Field of Classification Search
CPC ................................................ A61M 1/06–069
See application file for complete search history.

(56) References Cited

U.S. PATENT DOCUMENTS

2021/0093761 A1* 4/2021 Hwang ................. A61M 39/22

\* cited by examiner

*Primary Examiner* — Nathan R Price
*Assistant Examiner* — Courtney B Fredrickson

(57) ABSTRACT

The present disclosure discloses an assembling-facilitated breast pump, including, a main body, a milk flowing member and a breast cover; the main body includes a suction assembly and a milk storage container; the suction assembly is detachably connected to the milk storage container a negative pressure tank is arranged in the milk storage container; the suction assembly is communicated to the negative pressure tank; the entire main body is hemispherical; the milk flowing member is hermetically plugged, into the negative pressure tank; one end of the milk flowing member is provided with an opening; a side of the milk flowing member close to the opening is provided with a milk outlet; the milk outlet is used for being communicated to an accommodating cavity of the milk storage container; and a narrow end of the breast cover is hermetically plugged to the opening.

17 Claims, 9 Drawing Sheets

ASSEMBLING-FACILITATED BREAST PUMP

TECHNICAL FIELD

The present disclosure relates to the technical field of breast pumps, in particular to an assembling-facilitated breast pump.

BACKGROUND

A breast pump is a tool used for pumping out breast milk that has accumulated in breasts. It is generally used when a baby cannot directly breastfeed, or when the mother has a nipple problem, or when the mother still desires breastfeed while working.

There are many kinds of breast pumps. Currently, electric breast pumps are commonly used on the market. Such an electric breast pump usually includes a breast pump main unit, breast pump cups, negative pressure conducting members and feeding bottles. The feeding bottles, the breast pump cups and the breast pump unit are connected and fixed, through a three-way member; and the negative pressure conducting members are arranged between the breast pump main unit and the three-way member. This kind of breast pump has many accessories, so that it is difficult for a user to assemble the breast pump, and the breast pump is inconvenient to use. Meanwhile, there are many parts needing to be assembled in a closed way, so that problems such as an assembling mistake and air leakage easily occur, which affects the normal use of the breast pump. Furthermore, most of such breast pumps can only be used when a user stands or sits. Cleaning after use is also troublesome.

SUMMARY

In order to overcome the shortcomings of the prior art, the invention provides an assembling-facilitated breast pump which is easy to assemble and has the advantages of simple structure, convenient disassembly and easy cleaning.

The technical scheme adopted by the present disclosure to solve the technical problem is: an assembling-facilitated breast pump including a main body which includes a suction assembly and a milk storage container, wherein the suction assembly is detachably connected to the milk storage container; a negative pressure tank is arranged inside the milk storage container; the suction assembly is communicated with the negative pressure tank; the entire main body is, hemispherical; an arc-shaped outer surface of the main body is used for being fitted to an inner surface of the breast cover; a milk flowing member which is hermetically plugged to the negative pressure tank, wherein the milk flowing member is made of a deformable elastic material; one end of the milk flowing member is provided with an, opening; a side of the milk flowing member close to the opening is provided with a milk outlet; the milk outlet is used for being communicated to an accommodating cavity of the milk storage container; and a breast cover which is horn-shaped, wherein a narrow end of the breast cover is hermetically plugged to the opening.

In one embodiment, a check valve is arranged at the milk outlet; and the check valve is used for directionally allowing breast milk to flow from the milk flowing member into the milk storage container.

In one embodiment, the milk flowing member includes a columnar connecting portion and a conical deformation portion; the negative pressure tank is columnar; and when the milk flowing member is plugged to the negative pressure tank, an outer wall of the connecting portion is clung to an inner wall of the negative pressure tank.

In one embodiment, the deformation portion is provided with a deformation cavity communicated with the opening; the narrow end of the breast cover is provided with a milk inlet; when the narrow end of the breast cover is plugged to the opening, an outer wall of the narrow end of the breast cover is clung to an inner wall of the connecting portion; and the milk inlet is communicated to the deformation cavity.

In one embodiment, the inner wall of the connecting portion is provided with an open slot; the milk outlet is arranged at the open slot; and the open slot is used for communicating the milk outlet with the deformation portion.

In, one embodiment, a sealing block is provided on the outer wall of the narrow end of the breast cover in a protruding manner; and when the narrow end of the breast cover is plugged to the opening, the sealing block is plugged to the open slot.

In one embodiment, a side of the outer wall of the narrow end of the breast cover away from the sealing block is provided with a butting block; and when the narrow end of the breast cover is plugged to the opening, the butting block is butted against the inner wall of the connecting portion.

In one embodiment, the deformation portion is provided with supporting ribs; and the supporting ribs are arranged on a side wall of the deformation portion at intervals.

In one embodiment, an outer side of a wide end of the breast cover is provided with a clamping slot; a clamping block is provided at an edge of the main body in a protruding manner; and when the narrow end of the breast cover is plugged to the opening, the clamping block is clamped to the clamping slot, and the breast cover covers the accommodating cavity of the milk storage container.

In one embodiment, an inner wall of the accommodating cavity is provided with a through hole for communicating the accommodating cavity to the atmosphere; the main body is provided with a sealing cover; one end of the sealing cover is connected to an outer surface of the main body; and the other end of the sealing cover is detachably covered at the through hole.

In one embodiment, the milk storage container is provided with a first arc surface; the suction assembly is provided with a second arc surface; when the suction assembly is connected to the milk storage container, the first arc surface and the second arc surface form the arc-shaped outer surface; and the arc-shaped outer surface is used for being fitted to an inner surface of the breast cover.

In one embodiment, the suction assembly is provided with a suction port; an air guide column is provided on the milk storage container in a protruding manner; the air guide column is communicated to the negative pressure tank; and when the suction assembly is connected to the milk storage container, the suction port is communicated to the air guide column.

In one embodiment, a sealing ring is arranged in the suction port; when the suction assembly is connected to the milk storage container, an inner wall of the sealing ring is clung to a surface of an outer wall of the air guide column; and an outer wall of the sealing ring is clung to a side wall of the air guide column.

In one embodiment, the outer surface of the milk storage container is provided with a convex block; the outer surface of the suction assembly is provided with a groove; and when the suction assembly is connected to the milk storage container, the convex block is clamped to the groove.

In one embodiment, the outer surface of the milk storage container is provided with a plugging block; the outer surface of the suction assembly is provided with a plugging slot; and when the suction assembly is connected to the milk storage container, the plugging block is clamped to the plugging slot.

In one embodiment, the breast cover includes a plastic plugging portion and an elastic fitting portion; the plugging portion is located at the narrow end of the breast cover; and the fitting portion is located at the wide end of the breast cover.

In one embodiment, a side of the suction assembly facing towards the milk storage container is provided with a charging port; and when the suction assembly is connected to the milk storage container, the milk storage container is covered at the charging port.

The present disclosure also has the beneficial effects: due to the above structural arrangement, the suction assembly is communicated to the negative pressure tank, and the milk flowing member is hermetically plugged to the negative pressure tank. During use, a staged negative pressure generated by the suction assembly directly acts on the milk flowing member; the milk flowing member is deformed and reset stage by stage to generate a suction force, which suck breast milk. The narrow end of the horn-shaped breast cover is connected to the opening to accommodate the nipple of a user; and the wide end of the horn-shaped breast cover is smoothly transitioned, which is suitable for being fitted to the breast and keeping tight, thus effectively improving the efficiency of sucking breast milk and also providing a good use experience for a user. The milk outlet is arranged on the side of the milk flowing member close to the opening, so that when a user is in different states, such as standing, sitting, lying on the side and lying on the back, the breast milk in the milk flowing member can be ensured to flow out from the milk outlet and stored in the milk storage container. The elastic milk flowing member can achieve collection and flowing of the breast milk and can also generate and transmit a negative pressure. Meanwhile compared with a traditional breast pump, this breast pump has a simpler structure and requires a smaller number of accessories to be connected, so that such problems of poor air tightness, low milk suction efficiency, difficulty in cleaning and the like due to improper connection of accessories are effectively reduced. Moreover, the suction assembly can be detachably connected to the milk storage container, so that the suction assembly that contains many electrical elements can be removed during cleaning to prevent washing liquid from flowing into the suction assembly and ensure the service life of the suction assembly. In addition, when the suction assembly or the milk storage container is damaged by accident, the assembly can be replaced in time, which is convenient for a user; loss of the user is also reduced; and the service life of the breast pump is prolonged in another way.

DETAILED DESCRIPTION OF THE EMBODIMENTS

Figure 1:
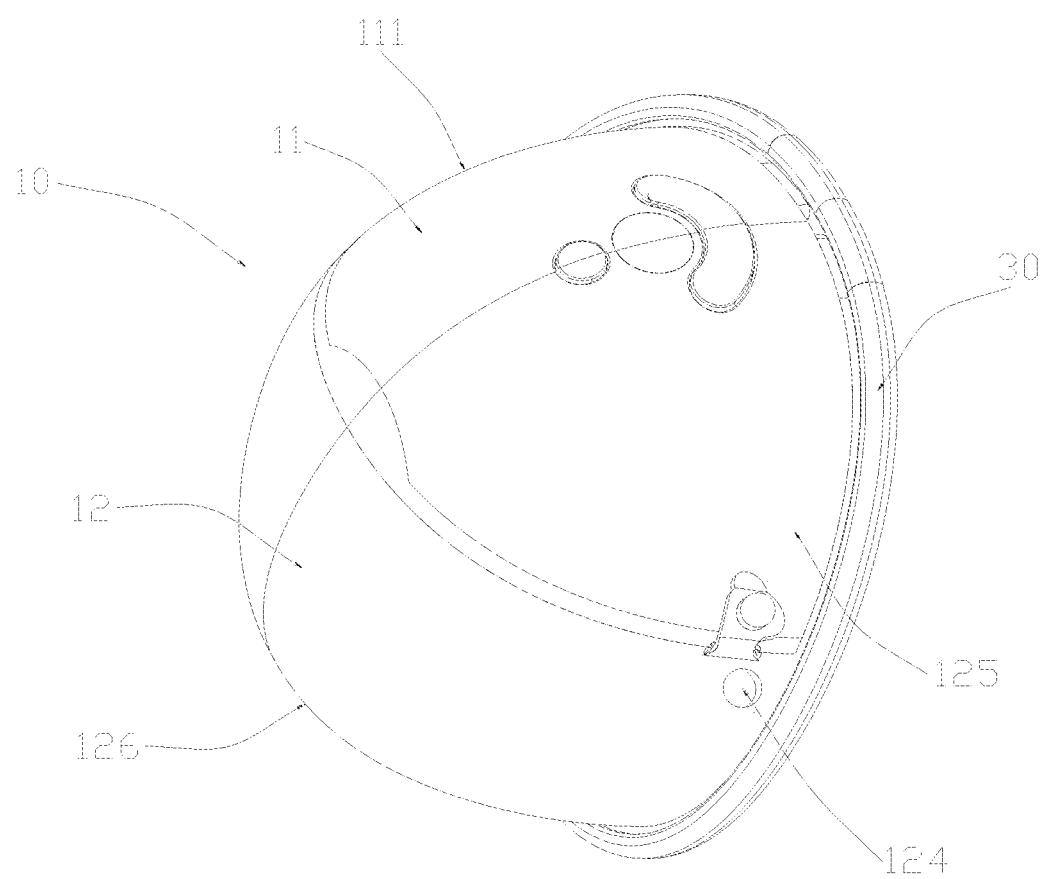
FIG. 1 is a schematic diagram of an entire structure in a first angle of the present disclosure.
Figure 2:
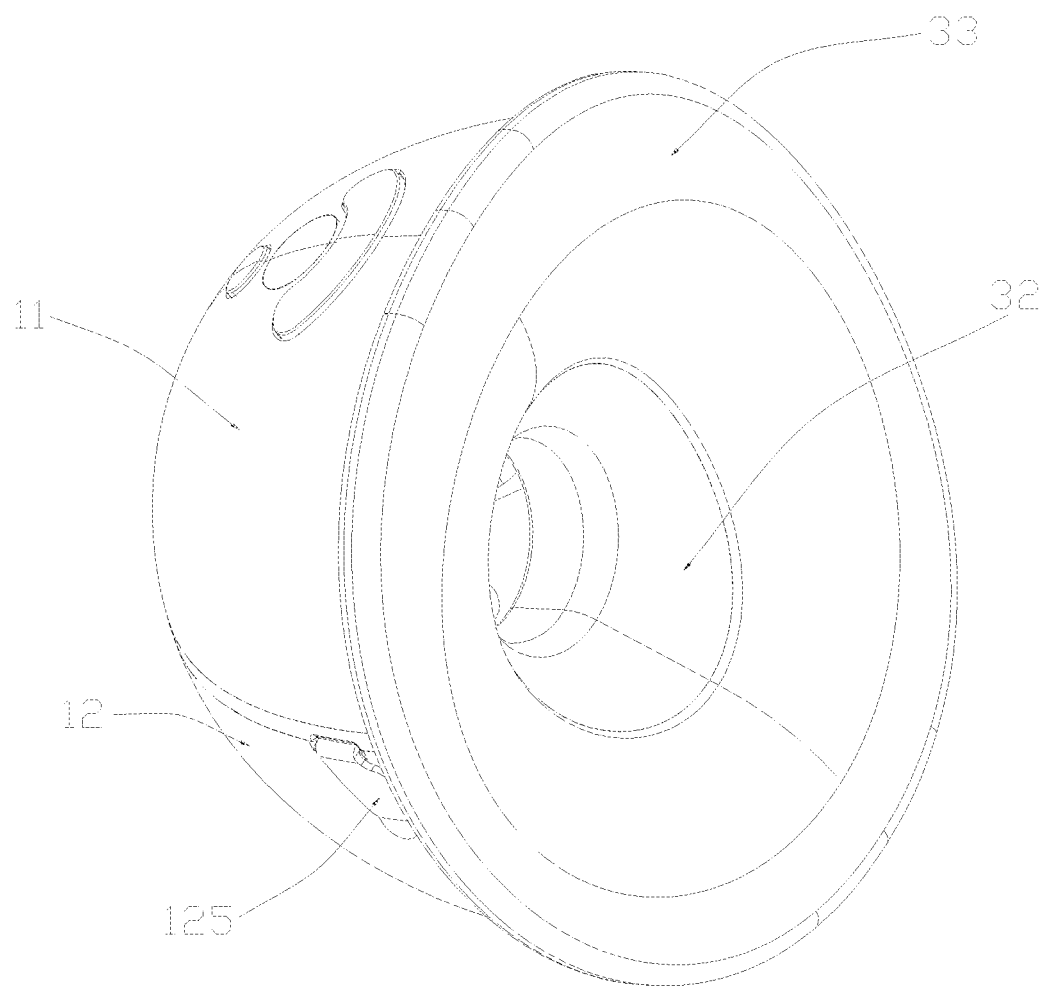
FIG. 2 is a schematic diagram of an entire structure in a second angle of the present disclosure.
Figure 3:
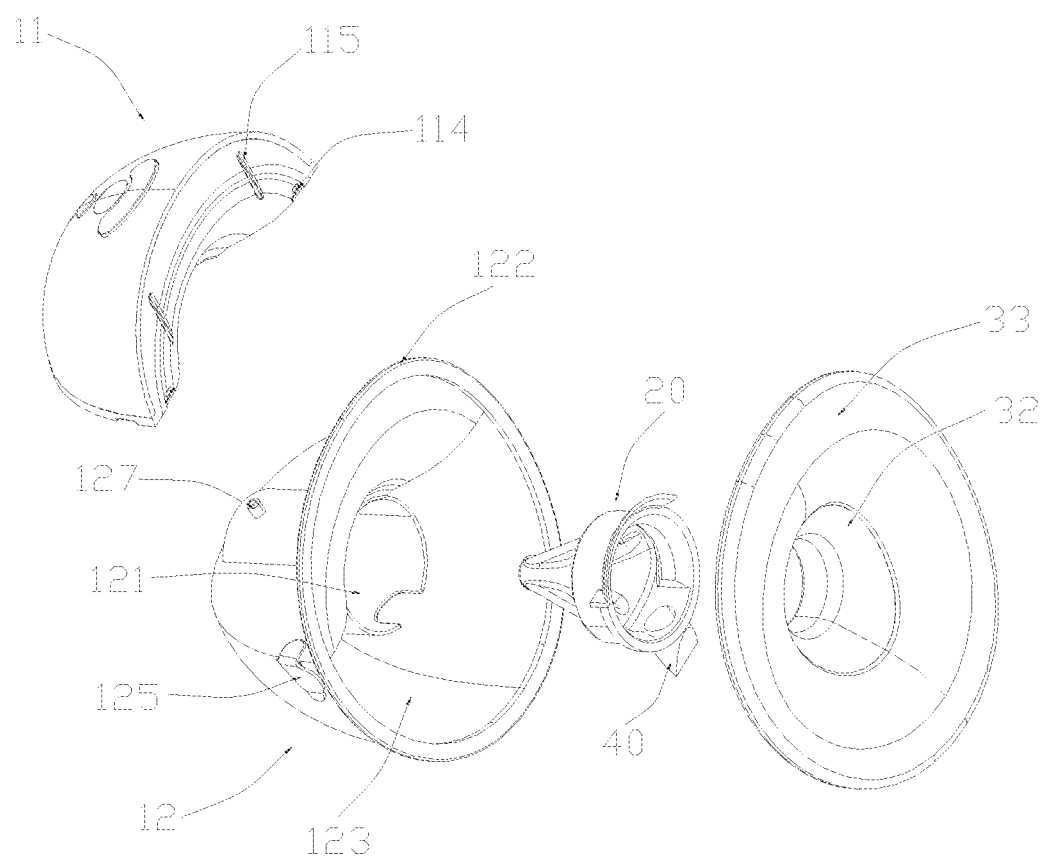
FIG. 3 is a schematic exploded structural diagram in a first angle of the present disclosure.
Figure 4:
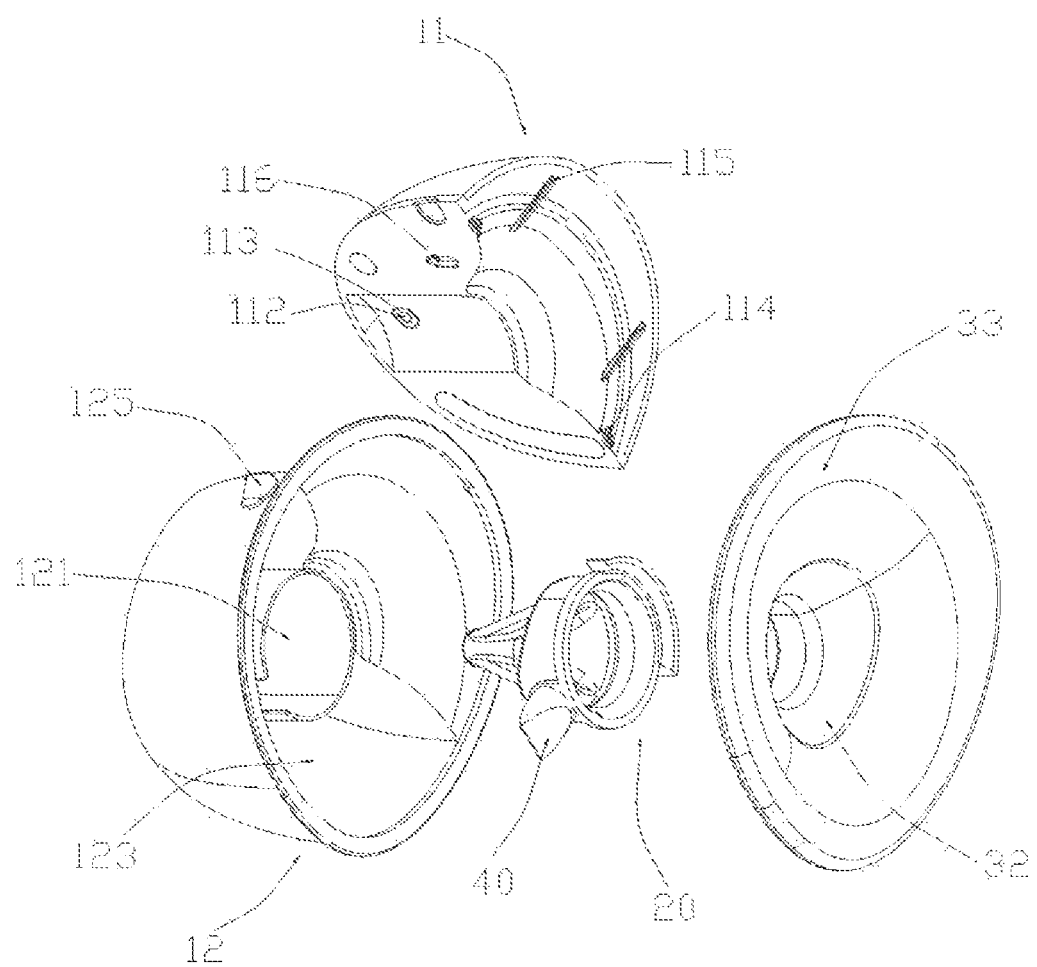
FIG. 4 is a schematic exploded structural diagram in a second angle of the present disclosure.
Figure 5:
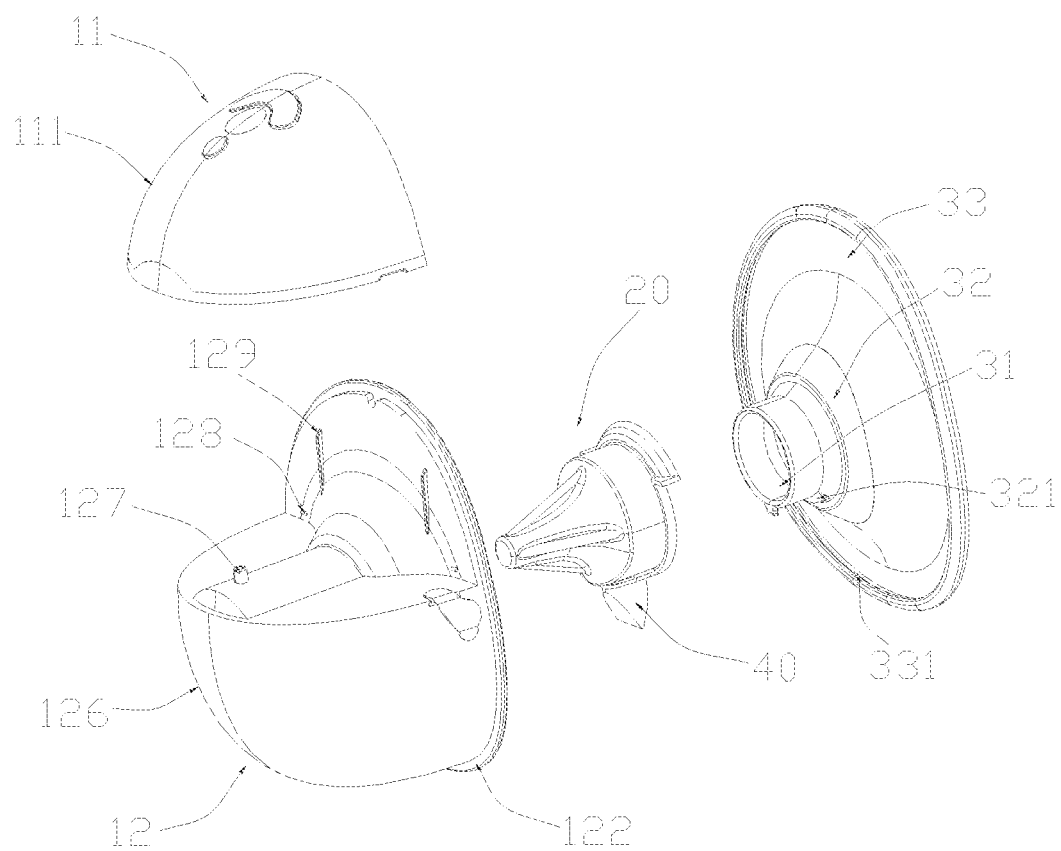
FIG. 5 is a schematic exploded structural diagram in a third angle of the present disclosure.
Figure 6:
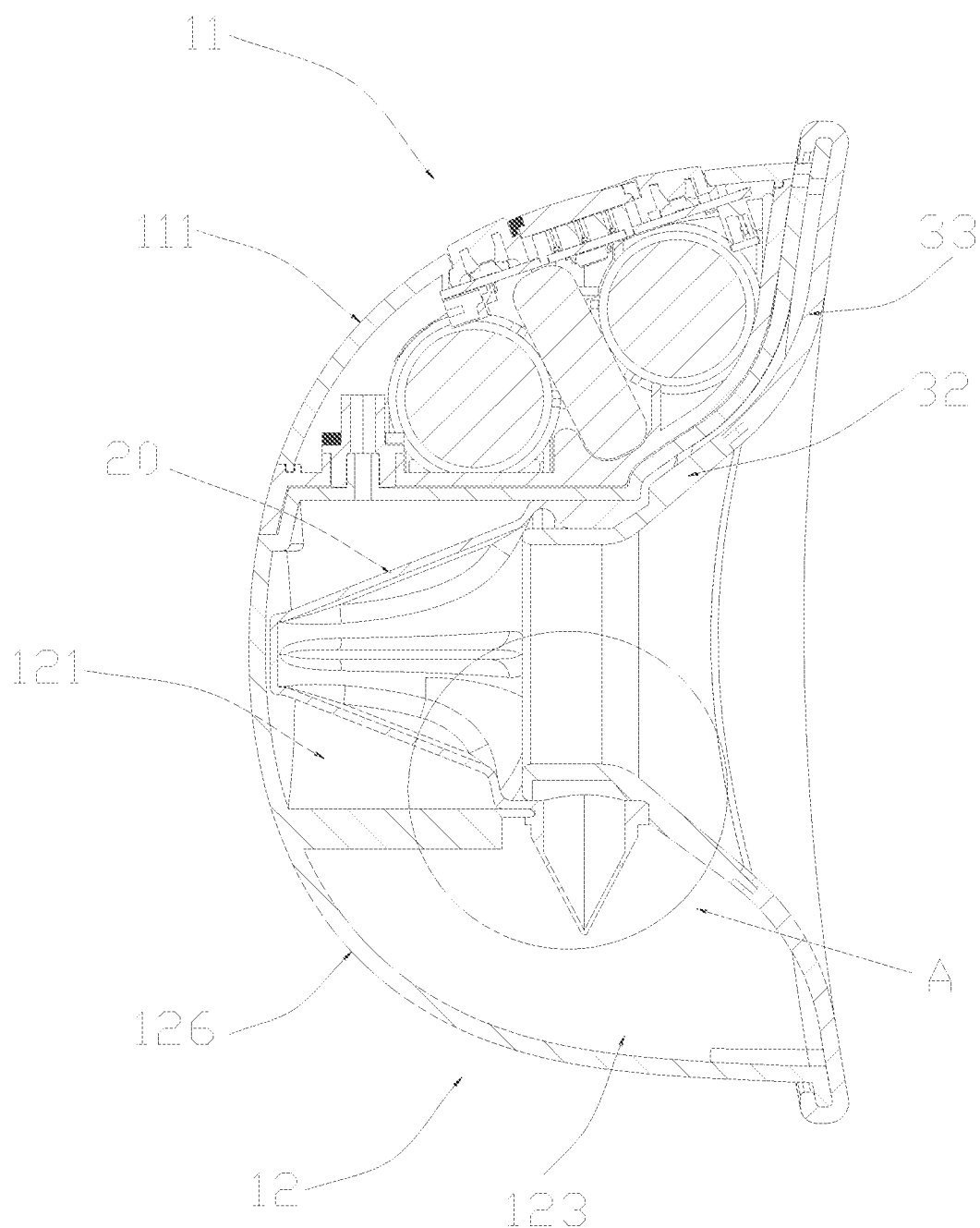
FIG. 6 is a schematic diagram of a sectional structure of the present disclosure.
Figure 7:
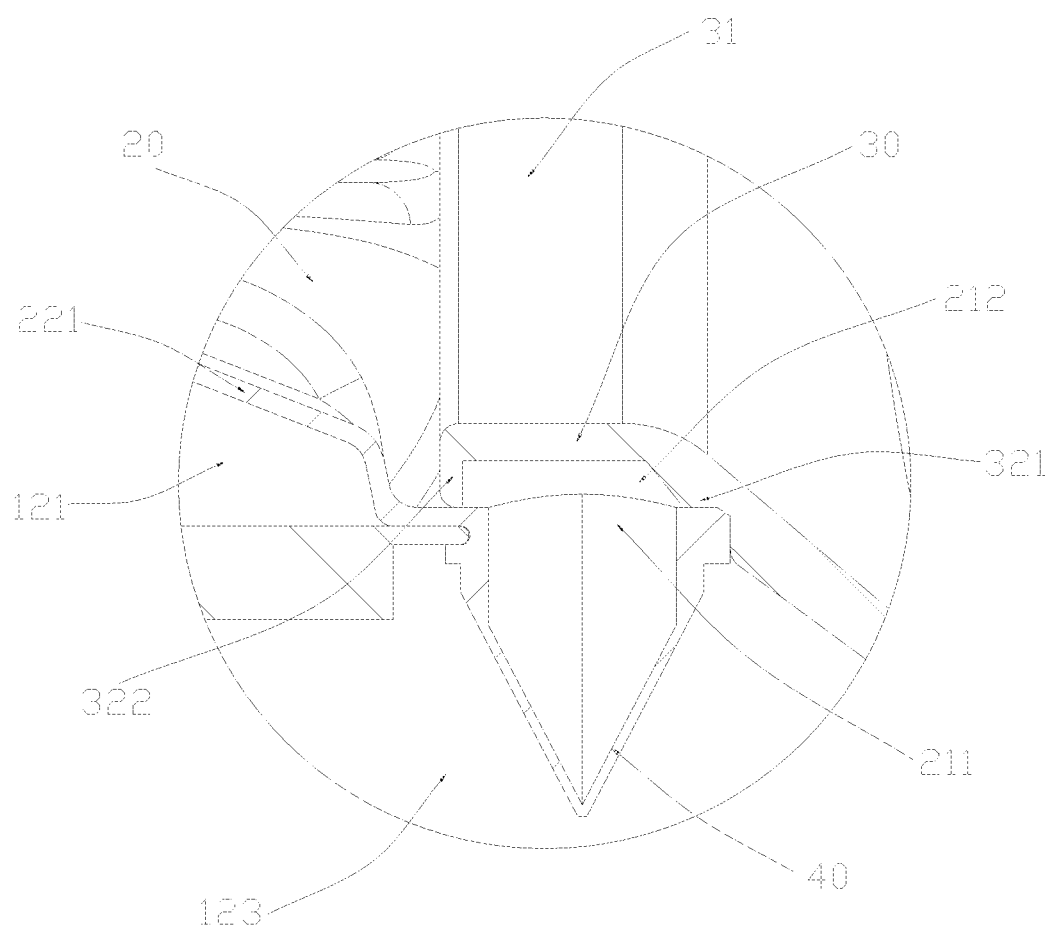
FIG. 7 is an enlarged diagram of circle A in FIG. 6.
Figure 8:
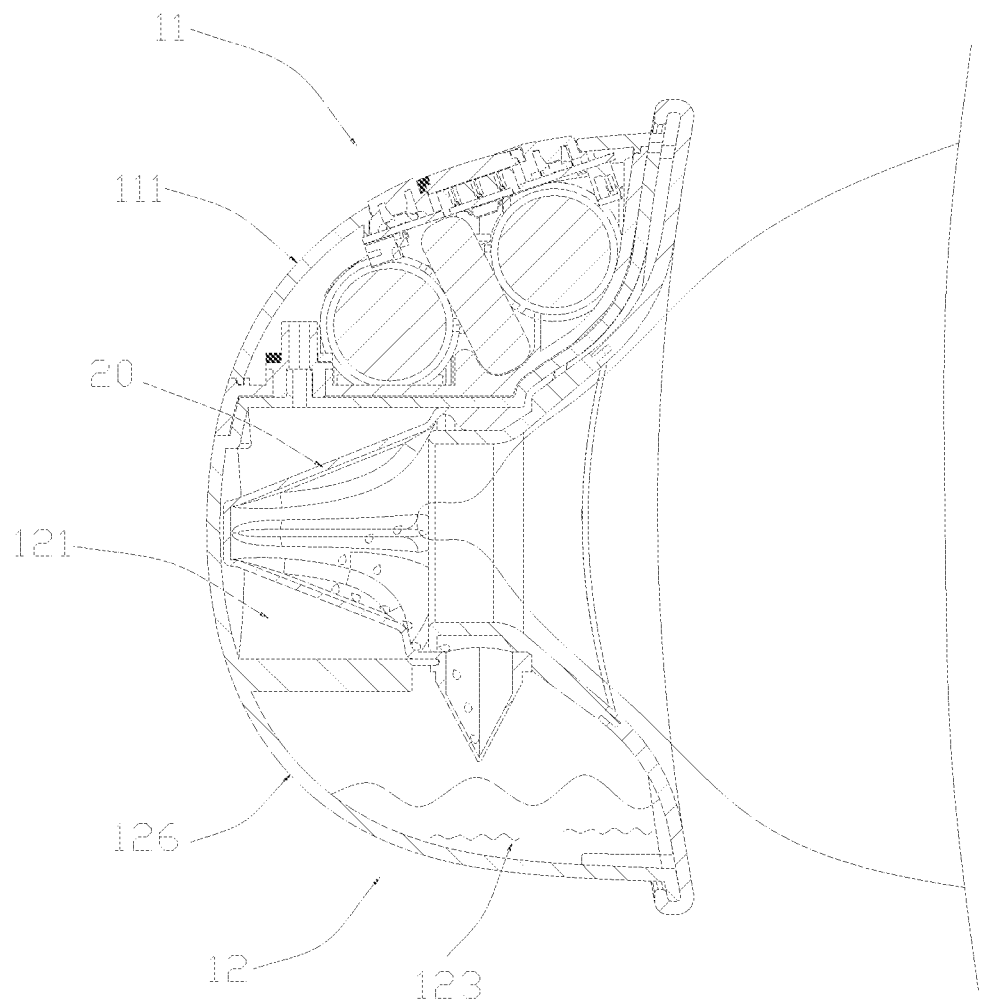
FIG. 8 is a schematic diagram of a sectional structure of a used state of the present disclosure.
Figure 9:
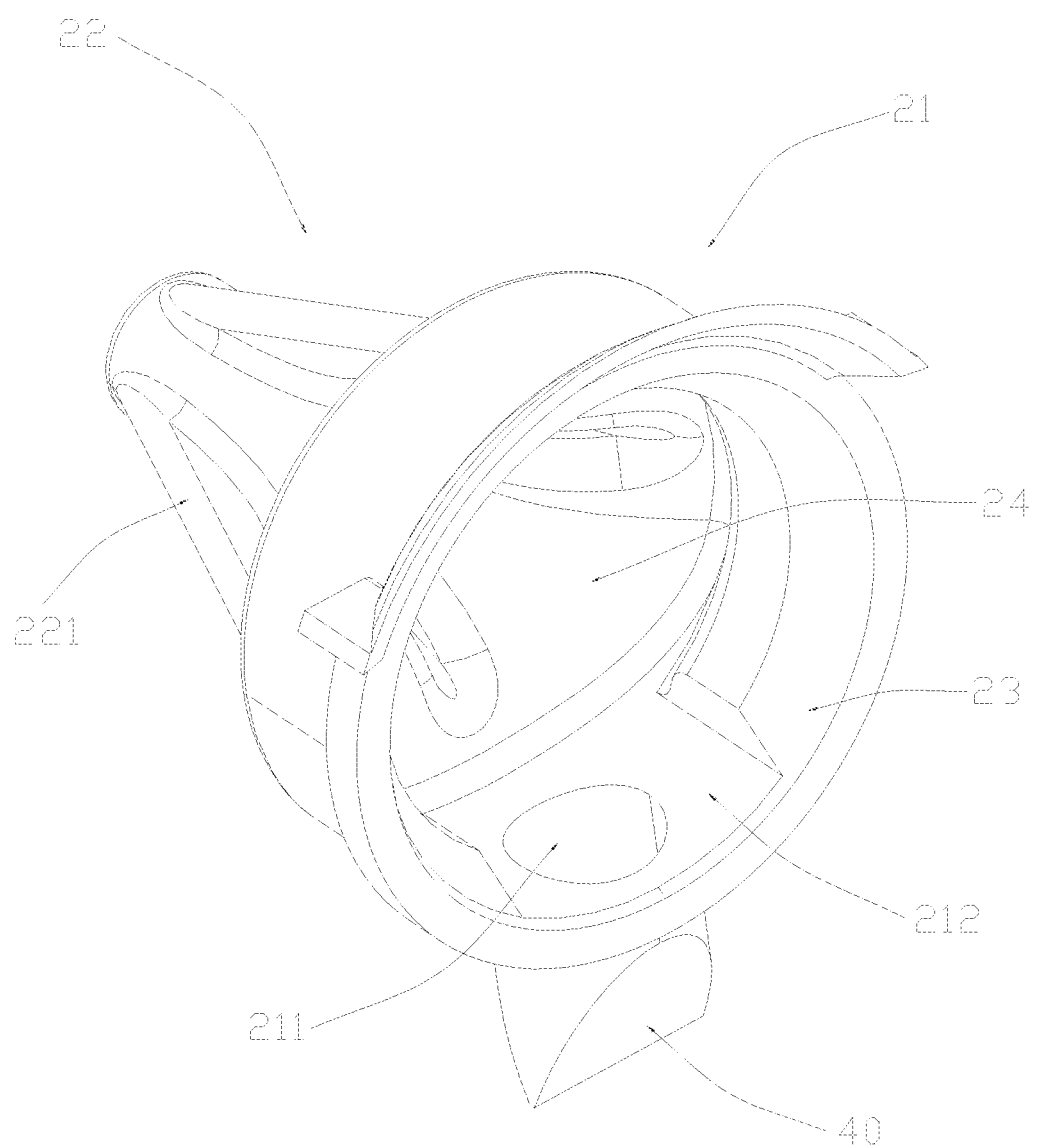
FIG. 9 is a schematic diagram of an entire structure of a milk flowing member of the present disclosure.

Referring to FIG. 1 to FIG. 9, an assembling-facilitated breast pump includes:

a main body 10 which includes a suction assembly 11 and a milk storage container 12, wherein the suction assembly 11 is detachably connected to the milk storage container 12; a negative pressure tank 121 is arranged inside the milk storage container 12: the suction assembly 11 is communicated with the negative pressure tank 121; the entire main body 10 is hemispherical; an arc-shaped outer surface of the main body 10 is used for being fitted to an inner surface of the breast cover;

a milk flowing member 20 which is hermetically plugged to the negative pressure tank 121, wherein the milk flowing member 20 is made of a deformable elastic material; one end of the milk flowing member 20 is provided with an opening 23; a side of the milk flowing member 20 close to the opening 23 is provided with a milk outlet 211; the milk outlet 211 is used for being communicated to an accommodating cavity 123 of the milk storage container 12; and a breast cover 30 which is horn-shaped, wherein a narrow end of the breast, cover 30 is hermetically plugged to the opening 23.

Due to the above structural arrangement, the suction assembly is communicated to the negative pressure tank, and the milk flowing member is hermetically plugged to the negative pressure tank. During use, a staged negative pressure generated by the suction assembly directly acts on the milk flowing member; the milk flowing member is deformed and reset stage by stage to generate a suction force, which suck breast milk. The narrow end of the horn-shaped breast cover is connected to the opening to accommodate the nipple of a user; and the wide end of the horn-shaped breast cover is smoothly transitioned, which is suitable for being fitted to the breast and keeping tight, thus effectively improving the efficiency of sucking breast milk and also providing a good use experience for a user. The milk outlet is arranged on the side of the milk flowing, member close to the opening, so that when a user is in different states, such as standing, sitting, lying on the side and lying on the back, the breast milk in the milk flowing member can be ensured to flow out from the milk outlet and stored in the milk storage container. The elastic milk flowing member can achieve collection and flowing of the breast milk and can also generate and transmit a negative pressure. Meanwhile, compared with a traditional breast pump, this breast pump has a simpler structure and requires a smaller number of accessories to be connected, so that such problems of poor air tightness, low milk suction efficiency, difficulty in cleaning and the like due to improper connection of accessories are effectively reduced. Moreover, the suction assembly can be detachably connected to the milk storage container, so that the suction assembly that contains many electrical elements can be removed during cleaning to prevent washing, liquid from flowing into the suction assembly and ensure the service life of the suction assembly. In addition, when the suction assembly or the milk storage container is damaged by accident, the assembly can be replaced in time, which is convenient for a user; loss of the user is also reduced; and the service life of the breast pump is prolonged in another way.

A check valve 40 is arranged at the milk outlet 211; and the check valve 40 is used for directionally allowing breast milk to flow from the milk flowing member 20 into the milk storage container. Due to the above structural arrangement, the arrangement of the check valve can ensure the directional flowing of the breast milk, so that the breast milk directionally flows from the milk flowing member to the milk storage container to improve the milk collection efficiency. Preferably, the check valve can be a duckbill valve. The duckbill valve has a simple and stable structure and a good effect, and the price is low.

The milk flowing member 20 includes a columnar connecting portion 21 and a conical deformation portion 22; the negative pressure tank 121 is columnar; and when the milk flowing member 20 is plugged to the negative pressure tank 121, an outer wall of the connecting portion 21 is clung to an inner wall of the negative pressure tank 121. Due to the above structural arrangement, the columnar connecting portion and the columnar negative pressure tank cooperate with each other, which is convenient for installation and removal and more easily achieves sealing. The outer wall of the connecting portion is clung to the inner wall of the negative pressure tank, so that the staged negative pressure generated by the suction assembly acts on the deformation portion to enable the deformation portion to be deformed/reset stage by stage, thus better sucking breast milk. Furthermore, the inner wall of the conical deformation portion is an inclined curved surface, so that the breast milk entering the deformation portion flows down under the action of the gravity and then flows out from the milk outlet, which further improves the milk collection efficiency. Even if a user lies on her side or back, it can still ensure that the breast milk can flow into the milk storage container. The breast pump is suitable for various usage scenarios and is convenient for a user.

The deformation portion 22 is provided with a deformation cavity 24 communicated with the opening 23; the narrow end of the breast cover 30 is provided with a milk inlet 31; when the narrow end of the breast cover 30 is plugged to the opening 23, an outer wall of the narrow end of the breast cover 30 is clung to an inner wall of the connecting portion 21; and the milk inlet 31 is communicated to the deformation cavity 24. Due to the above structural arrangement, the outer wall of the narrow end of the breast cover is clung to the inner wall of the connecting portion to achieve tight fitting between the breast cover and the milk flowing member. The milk inlet is communicated to the deformation cavity of the milk flowing member, so that the breast milk can flow into the deformation cavity, flow out via the milk outlet, and be stored in the milk storage container.

The inner wall of the connecting portion 21 is provided with an open slot 212; the milk outlet 211 is arranged at the open slot 212; and the open slot 212 is used for communicating the milk outlet 211 with the deformation portion 24. Due to the above structural arrangement, the open slot is arranged on the inner wall of the connecting portion, so that the milk outlet can be allowed, to be communicated with the deformation cavity to ensure that the breast milk in the deformation cavity can effectively flow out via the milk outlet, which improves the flowing efficiency of the breast milk, thus enhancing the use experience of a user.

A sealing block 321 is provided on the outer wall of the narrow end of the breast cover 30 in a protruding manner; and when the narrow end of the breast cover 30 is plugged to the opening 23, the sealing block 321 is plugged to the open slot 212. Due to the above structural arrangement, the sealing block is plugged to the open slot, which can ensure the air tightness of the breast pump and prevent air or breast milk from flowing in or flowing out from the open slot. It ensures that the milk outlet is communicated to the deformation cavity and can also ensure the air tightness of the breast pump. The breast pump has a simple structure and is practical.

A side of the outer wall of the narrow end of the breast cover 30 away from the sealing block 321 is provided with a butting block 322; and when the narrow end of the breast cover 30 is plugged to the opening 23, the butting block 322 is butted against the inner wall of the connecting portion 21. Due to the above structural arrangement, the butting block is butted against the inner wall of the connecting portion, so that the outer wall of the connecting portion and the inner wall of the negative pressure tank are connected, more tightly, which further improves the air tightness of the breast pump. The butting block, the outer wall of the narrow end of the breast cover and the sealing block form a bridge-shaped structure, and a flowing channel is formed above the milk outlet, which ensures communication between the milk outlet and the negative pressure cavity and improves the milk collection, and flowing efficiency.

The deformation portion 22 is provided with supporting ribs 221; and the supporting ribs 221 are arranged on a side wall of the deformation portion 22 at intervals. Due to the above structural arrangement, the supporting ribs have a stable structure. Under the action of the suction assembly, the supporting ribs deform little, so that the basic conical shape of the deformation portion can be maintained. During use, the nipples of most users are placed in the plugging portion, but some users have longer nipples, so the front parts of the nipples may possibly extend into the deformation portion. The supporting ribs can better protect the nipples of such users, and the deformation portion can be kept in the basic shape, which prevents the deformation portion from clamping the nipples during the staged deformation and brings a better use experience to users. Furthermore, the deformation portion is kept in the basic conical structure, and the inclined surface of the inner wall of the deformation portion can also be ensured to accelerate the flowing of the breast milk in the deformation cavity and empty the deformation cavity as fast as possible, so as to better collect the breast milk.

An outer side of a wide end of the breast cover 30 is provided with a clamping slot 331; a clamping block 122 is provided at an edge of the main body 10 in a protruding manner; and when the narrow end of the breast cover 30 is plugged to the opening 23, the clamping block 122 is clamped to the clamping slot 331, and the breast cover 30 covers the accommodating cavity 123 of the milk storage container 12. Due to the above structural arrangement, the clamping block is clamped to the clamping slot, which can achieve tight fitting between the edge of the main body and the edge of the breast cover, so that the breast pump is formed into a stable whole, and the stability of the breast pump is improved. Furthermore, this structure is convenient for assembling and disassembling, so that, it is convenient for a user to disassemble the breast pump for cleaning or to assemble the breast pump for use. In addition, covering the breast cover to the accommodating cavity can ensure the air tightness of the accommodating cavity, which effectively makes use of the space of the breast pump and reduces the volume of the breast pump; and it is convenient for a user to puts the breast pump into the breast cover, which relieves both hands of the user. The milk storage container itself has a connection function, so that it is knot necessary to add a connecting assembly, thus reducing the operating steps of a user and facilitating user's use. In addition, the number of components to be cleaned is reduced, and the use experience of a user is effectively enhanced.

An inner wall of the accommodating cavity 123 is provided with a through hole 124 for communicating the accommodating cavity 123 to the atmosphere; the main body 10 is provided with a sealing cover 125; one end of the sealing cover 125 is connected to an outer surface of the main body; and the other end of the sealing cover 125 is detachably covered at the through hole 124. Due to the above structural arrangement, during use, the sealing cover is covered at the through hole, which ensures the air tightness of the breast pump and prevents the breast milk from flowing out via the through hole. After breast milk is collected, the sealing cover is uncovered, and the breast milk in the accommodating cavity can be poured out from the through hole, which greatly facilitates user's use.

The milk storage container 12 is provided with a first arc surface 126; the suction assembly 11 is provided with a second arc surface 111; when the suction assembly 11 is connected to the milk storage container 12, the first arc surface 126 and the second arc surface 111 form the arc-shaped outer surface; and the arc-shaped outer surface is used for being fitted to an inner surface of the breast cover. Due to the above structural arrangement, the first arc surface and the second arc surface form the smooth arc-shaped outer surface, so that it can be convenient for a user to place the breast pump into the breast cover to relieve both hands of the user, and the user is allowed to do other work while using the breast pump. In addition, the arc-shaped outer surface is better fitted to the inner surface of the breast cover, which can also prevent the breast, pump from falling off and improve the stability, safety and convenience of use of the breast pump.

The suction assembly 11 is provided with a suction port 112; an air guide column 127 is provided on the milk storage container 12 in a protruding manner; the air guide column 127 is communicated to the negative pressure tank 121; and when the suction assembly 11 is connected to the milk storage container 12, the suction port 112 is communicated to the air guide column 127. Due to the above structural arrangement, the air guide column is plugged to the suction port, so that on the one hand, communication between the suction portion and the air guide column is achieved, thus achieving communication between the suction assembly and the negative pressure tank; and on the other hand, the air guide column can also be prevented from being separated from the suction assembly, which improves the stability of the breast pump and facilitates user's use.

A sealing ring 113 is arranged in the suction port 112; when the suction assembly 11 is connected to the milk storage container 12, an inner wall of the sealing ring 113 is clung to a surface of an outer wall of the air guide column 127; and an outer wall of the sealing ring 113 is clung to a side wall of the air guide column 127. Due to the above structural arrangement, the sealing ring is elastic. When the suction assembly is connected to the milk storage container, the air guide column is plugged into the suction port, and the sealing ring can effectively seal a gap between the air guide column and the suction port and ensure the air tightness of the breast pump. Meanwhile, the air guide column can also be fixed, thus fixing the suction assembly and preventing the suction assembly and the milk storage container from moving along a horizontal direction.

The outer surface of the milk storage container 12 is provided with a convex block 128; the outer surface of the suction assembly 11 is provided with a groove 114; and when the suction assembly 11 is connected to the milk storage container 12, the convex block 128 is clamped to the groove 114. Due to the above structural arrangement, the convex block is clamped to the groove, so that fixing of the milk storage container and the suction assembly can be achieved, which prevents the suction assembly and the milk storage container from moving along a vertical direction, effectively improves the stability of the breast pump and facilitates a user to install and remove the suction assembly.

The outer surface of the milk storage container 12 is provided with a plugging block 129; the outer surface of the suction assembly 11 is provided with a plugging slot 115; and when the suction assembly 11 is connected to the milk storage container 12, the plugging block 129 is clamped to the plugging slot 115. Due to the above structural arrangement, by the arrangement of the plugging block and the plugging slot, the milk storage container and the suction assembly can be further fixed. Furthermore, the plugging block gradually becomes wide from bottom to top, so that it is more convenient for a user in a plugging process. The plugging block can slide to a mounting position along the plugging slot, which is safe and more stable.

The breast cover 30 includes a plastic plugging portion 32 and an elastic fitting portion 33; the plugging portion 32 is located at the narrow end of the breast cover 30; and the fitting portion 33 is located at the wide end of the breast cover 30. Due to the above structural arrangement, the plastic plugging portion can cause the connection of the plugging portion, the milk flowing member and the negative pressure tank to be more stable; the outer surface of the plugging portion is clung to the inner surface of the milk flowing member; the inner wall of the negative pressure tank is clung to the outer surface of the milk flowing member; the side wall of the milk flowing member is clamped between the plugging portion and the negative pressure tank, so that the structure of the breast pump is more stable; the elastic fitting portion can have a certain deformation, so that when the clamping block is clamped to the clamping slot, the deformation of the fitting portion is helpful for installation or removal by a user and facilitates user's operation. The elastic fitting portion is fitted to the breast of a user, which makes the user feel more comfortable; and the use experience of the user is enhanced.

A side of the suction assembly 11 facing towards the milk storage container 12 is provided with a charging port 116; and when the suction assembly 11 is connected to the milk storage container 12, the milk storage container 12 is covered at the charging port 116. Due to the above structural arrangement, the charging port is arranged on the side of the suction assembly facing towards the milk storage container. When the suction assembly and the milk storage container are assembled, the charging port can be effectively hidden and is prevented from being exposed, so that water, dust and other impurities are effectively prevented from entering the charging port, which ensures the use of the breast pump.

What is claimed is:
1. An assembling-facilitated breast pump, comprising:
a main body which comprises a suction assembly and a milk storage container, wherein the suction assembly is detachably connected to the milk storage container; a negative pressure tank is arranged inside the milk storage container; the suction assembly is communi- cated with the negative pressure tank; the entire main body is hemispherical and comprises an arc-shaped outer surface;

a milk flowing member which is hermetically plugged to the negative pressure tank, wherein the milk flowing member is made of a deformable elastic material; one end of the milk flowing member is provided with an opening; a side of the milk flowing member close to the opening is provided with a milk outlet; the milk outlet is used for being communicated to an accommodating cavity of the milk storage container; and a breast cover which is horn-shaped, wherein a narrow end of the breast cover is hermetically plugged to the opening.

2. The assembling-facilitated breast pump according to claim 1, wherein a check valve is arranged at the milk outlet; and the check valve is used for directionally allowing breast milk to flow from the milk flowing member into the milk storage container.

3. The assembling-facilitated breast pump according to claim 1, wherein the milk flowing member comprises a columnar connecting portion and a conical deformation portion; the negative pressure tank is columnar; and when the milk flowing member is plugged to the negative pressure tank, an outer wall of the connecting portion is clung to an inner wall of the negative pressure tank.

4. The assembling-facilitated breast pump according to claim 3, wherein the deformation portion is provided with a deformation cavity communicated with the opening; the narrow end of the breast cover is provided with a milk inlet; when the narrow end of the breast cover is plugged to the opening, an outer wall of the narrow end of the breast cover is clung to an inner wall of the connecting portion; and the milk inlet is communicated to the deformation cavity.

5. The assembling-facilitated breast pump according to claim 4, wherein the inner wall of the connecting portion is provided with an open slot; the milk outlet is arranged at the open slot; and the open slot is used for communicating the milk outlet with the deformation portion.

6. The assembling-facilitated breast pump according to claim 5, wherein a sealing block is provided on the outer wall of the narrow end of the breast cover in a protruding manner; and when the narrow end of the breast cover is plugged to the opening, the sealing block is plugged to the open slot.

7. The assembling-facilitated breast pump according to claim 6, wherein a side of the outer wall of the narrow end of the breast cover away from the sealing block is provided with a butting block; and when the narrow end of the breast cover is plugged to the opening, the butting block is butted against the inner wall of the connecting portion.

8. The assembling-facilitated breast pump according to claim 3, wherein the deformation portion is provided with supporting ribs; and the supporting ribs are arranged on a side wall of the deformation portion at intervals.

9. The assembling-facilitated breast pump according to claim 1, wherein an outer side of a wide end of the breast cover is provided with a clamping slot; a clamping block is provided at an edge of the main body in a protruding manner; and when the narrow end of the breast cover is plugged to the opening, the clamping block is clamped to the clamping slot, and the breast cover covers the accommodating cavity of the milk storage container.

10. The assembling-facilitated breast pump according to claim 1, wherein an inner wall of the accommodating cavity is provided with a through hole for communicating the accommodating cavity to the atmosphere; the main body is provided with a sealing cover; one end of the sealing cover is connected to an outer surface of the main body; and the other end of the sealing cover detachably covers the through hole.

11. The assembling-facilitated breast pump according to claim 1, wherein the milk storage container is provided with a first arc surface; the suction assembly is provided with a second arc surface; when the suction assembly is connected to the milk storage container, the first arc surface and the second arc surface form the arc-shaped outer surface.

12. The assembling-facilitated breast pump according to claim 1, wherein the suction assembly is provided with a suction port; an air guide column is provided on the milk storage container in a protruding manner; the air guide column is communicated to the negative pressure tank; and when the suction assembly is connected to the milk storage container, the suction port is communicated to the air guide column.

13. The assembling-facilitated breast pump according to claim 12, wherein a sealing ring is arranged in the suction port.

14. The assembling-facilitated breast pump according to claim 1, wherein the outer surface of the milk storage container is provided with a convex block; the outer surface of the suction assembly is provided with a groove; and when the suction assembly is connected to the milk storage container, the convex block is clamped to the groove.

15. The assembling-facilitated breast pump according to claim 1, wherein the outer surface of the milk storage container is provided with a plugging block; the outer surface of the suction assembly is provided with a plugging slot; and when the suction assembly is connected to the milk storage container, the plugging block is clamped to the plugging slot.

16. The assembling-facilitated breast pump according to claim 1, wherein the breast cover comprises a plastic plugging portion and an elastic fitting portion; the plugging portion is located at the narrow end of the breast cover; and the fitting portion is located at the wide end of the breast cover.

17. The assembling-facilitated breast pump according to claim 1, wherein a side of the suction assembly facing towards the milk storage container is provided with a charging port; and when the suction assembly is connected to the milk storage container, the milk storage container covers the charging port.

* * * * *